United States Patent
Kiesele et al.

(10) Patent No.: US 7,175,753 B2
(45) Date of Patent: Feb. 13, 2007

(54) PROCESS AND DEVICE FOR MONITORING THE HYDROGEN CONCENTRATION

(75) Inventors: Herbert Kiesele, Lübeck (DE); Peter Tschuncky, Lübeck (DE)

(73) Assignee: Drägerwerk Aktiengesellschaft (DE)

( * ) Notice: Subject to any disclaimer, the term of this patent is extended or adjusted under 35 U.S.C. 154(b) by 566 days.

(21) Appl. No.: 10/349,276

(22) Filed: Jan. 22, 2003

(65) Prior Publication Data

US 2003/0192781 A1    Oct. 16, 2003

(30) Foreign Application Priority Data

Apr. 11, 2002   (DE) ................ 102 15 909

(51) Int. Cl.
*G01N 27/26* (2006.01)
(52) U.S. Cl. .............. 205/775; 205/782; 204/406; 204/412; 204/431
(58) Field of Classification Search ............. None
See application file for complete search history.

(56) References Cited

U.S. PATENT DOCUMENTS

| | | | |
|---|---|---|---|
| 5,932,079 A * | 8/1999 | Haupt et al. ............ | 204/415 |
| 5,958,214 A * | 9/1999 | Nikolskaja ............... | 205/784 |
| 6,428,665 B1 * | 8/2002 | Ilic et al. ................. | 204/415 |
| 6,558,519 B1 * | 5/2003 | Dodgson et al. ......... | 204/401 |
| 6,896,781 B1 * | 5/2005 | Shen et al. ............... | 204/415 |
| 6,908,536 B2 * | 6/2005 | Beckmann ................ | 204/412 |
| 6,921,475 B2 * | 7/2005 | Kuhr et al. ............... | 205/775 |

FOREIGN PATENT DOCUMENTS

DE    197 26 453    8/2000

* cited by examiner

*Primary Examiner*—Alan Diamond
*Assistant Examiner*—Anthony Fick
(74) *Attorney, Agent, or Firm*—McGlew & Tuttle, PC

(57) ABSTRACT

A process and a device are provided for monitoring the hydrogen concentration in a gas with at least one device, which comprises an electrochemical gas sensor and a bipotentiostat, e.g., for use in internal combustion engines with hydrogen, in fuel cells and in the petrochemical industry. The electrochemical gas sensor used has two working electrodes (3) and (4), with which the hydrogen and oxygen concentrations are determined in the gas in different steps due to the application of a voltage by a bipotentiostat (5-18). In an additional, optional step, a voltage in the range of −1,100 mV to −800 mV is applied to a working electrode (4), so that hydrogen is formed at the working electrode (4) and the functional surface of the working electrode (4) as well as the sensitivity of the working electrode (3) to hydrogen can be checked. A cyclic repetition of the process steps, preferably offset in time, with two devices makes possible the continuous monitoring of the hydrogen and oxygen concentrations with regular checking of the working electrodes (3, 4) for their readiness to function.

20 Claims, 2 Drawing Sheets

PROCESS AND DEVICE FOR MONITORING THE HYDROGEN CONCENTRATION

FIELD OF THE INVENTION

The present invention pertains to a process and a device for monitoring the hydrogen concentration in a gas mixture.

BACKGROUND OF THE INVENTION

An electrochemical oxygen sensor with two working electrodes called a measuring electrode and a protective electrode, a counterelectrode called an auxiliary electrode, as well as a reference electrode is described in DE 197 26 453 C2. The measuring electrode, the protective electrode and the auxiliary electrode are arranged plane-parallel to one another with mats introduced between them, which are impregnated with an electrolyte and act as separators. The sensitivity of the sensor to vibration is considerably reduced by this type of arrangement. The electrolyte with the electrodes located in it is screened from the gas to be measured via a diffusion membrane consisting of polytetrafluoroethylene. All electrodes used are made of the same material, e.g., gold, platinum or alloys thereof An electrochemical gas sensor with a diffusion membrane consisting of a polymer containing bis-2,2-trifluoromethyl-4,5-difluoro-1,3-dioxol, especially a copolymer from the monomers bis-2,2-trifluoromethyl-4,5-difluoro-1,3-dioxol and tetrafluoroethylene (trademark "Teflon® AF") has been known from DE 200 22 508 U1. Shorter response time and improved sensitivity to gases such as oxygen and hydrogen can be observed during the measurement with such diffusion membranes.

SUMMARY OF THE INVENTION

The object of the present invention is to provide a process and a device that make possible the monitoring of the hydrogen concentration in a gas mixture and in which the readiness to function of the device is checked at the same time. In addition, it is possible to monitor the oxygen concentration.

According to the invention, a process is provided for monitoring the hydrogen concentration in a gas mixture with at least one first device comprising an electrochemical gas sensor, with the following steps forming a measuring cycle, the process beginning with one of the indicated steps. A voltage in a potential range I bringing about the oxidation of hydrogen is applied to the first working electrode via a first operational amplifier, and a voltage in a potential range II bringing about the reduction of oxygen is applied to a second working electrode via a second operational amplifier. The current conduction proportional to the concentration of hydrogen is measured at the first working electrode, and the current conduction proportional to the concentration of oxygen is measured at the second working electrode, and it is sent as a signal to the microcontroller and is compared with a preset signal value there. A voltage in the potential range II bringing about the reduction of oxygen is applied to the two working electrodes via the first and second operational amplifiers. The current conduction proportional to the concentration of oxygen is measured at the first and second working electrodes and is sent as a signal to the microcontroller and is compared with preset signal values there. The connection between the first operational amplifier and the first working electrode is interrupted by opening a first switch, and the open circuit potential is determined at the first working electrode and is sent as a signal to the microcontroller by means of an instrument amplifier and is compared with a preset signal value there, and a voltage in the potential range II bringing about the reduction of oxygen is applied to the second working electrode via the second operational amplifier. The current conduction proportional to the concentration of the oxygen is measured at the second working electrode and is sent as a signal to the microcontroller and is compared with a preset signal value there.

According to another aspect of the invention, a device for carrying out the process is provided with a first working electrode of an electrochemical gas sensor of the first and/or second device covering the potential range I with 0 mV to 200 mV and the potential range II with −700 mV to −300 mV and containing a measuring device for determining the "open circuit potential." A second working electrode covers the potential range II with −700 mV to −300 mV as well as the potential range III with −1,100 mV to −800 mV.

The process for monitoring the hydrogen concentration in a gas mixture containing oxygen uses the at least one first device comprising an electrochemical gas sensor. The electrochemical gas sensor used has two working electrodes, including a first, gas-side working electrode and a second, electrolyte-side working electrode, as well as a reference electrode and a counterelectrode. The working electrodes operate from time to time as anodes and as cathodes depending on how voltage is applied to them via a bipotentiostat. The bipotentiostat is actuated by a microcontroller and has as additional components three operational amplifiers, which are arranged upstream of one of the two working electrodes and the reference electrode. Precision resistors are connected in parallel to the two operational amplifiers belonging to the working electrodes.

Due to the suitable actuation of the device by the microcontroller, the hydrogen and oxygen concentrations in a gas mixture can be determined alternatingly with the process and the readiness of the device to function can be monitored.

This is advantageous, e.g., for the measurement of hydrogen in internal combustion engines, fuel cells or in the chemical industry, e.g., in the petrochemical industry. Since hydrogen may explode even at a low concentration in the air (lower explosion limit: 4%), the hydrogen concentration must be monitored continuously and reliably at least in closed spaces. In addition, due to the monitoring of the oxygen concentration, the process according to the present invention makes it possible to assess the quality of the air, e.g., for the protection of persons or in the interior space of a motor vehicle powered with hydrogen. The gas to be measured is fed to the electrochemical gas sensor, e.g., via a diffusion membrane.

Polytetrafluoroethylene (Teflon®) and perfluoroalkoxy (PFA), each in a layer thickness between 3 μm and 15 μm, as well as Teflon® AF (see above) in a layer thickness between 15 μm and 35 μm are suitable as materials for the diffusion membrane. As an alternative to a diffusion membrane, it is possible to feed the gas to be measured into the electrochemical gas sensor via capillaries, which have a diameter of about 10 μm to 50 μm and a length of 100 μm to 500 μm. A mixture of platinum and polytetrafluoroethylene is preferably used as the material for the electrodes.

The process according to the present invention comprises a sequence of a plurality of steps forming a measuring cycle.

In a first step (a) of a measuring cycle, a voltage in a potential range I bringing about the oxidation of hydrogen, preferably between 0 mV and 200 mV, is applied to the first working electrode via a first operational amplifier. These and all further data on potential ranges are related to a platinum-platinum oxide pseudo-reference electrode. At the same time, a voltage in a potential range II bringing about the reduction of oxygen, preferably between −700 mV and −300 mV, is applied to the second working electrode via a second operational amplifier. The current conduction caused by the oxidation of hydrogen at the first working electrode generates a signal that is proportional to the hydrogen concentration. The current conduction generated by the reduction of oxygen likewise generates a signal proportional to the oxygen concentration at the second working electrode. Both signals are sent to the microcontroller and are compared with preset signal values there.

In a second step (b), a voltage in the potential range II bringing about the reduction of oxygen is applied to both working electrodes via the first and second operational amplifiers. The current conduction proportional to the oxygen concentration is measured at the first and second working electrodes, sent as a signal to the microcontroller, and compared with preset signal values there. In a third step (c), the connection of the first operational amplifier to the first working electrode is interrupted by a first switch arranged between the first operational amplifier and the first working electrode being opened. The so-called "open circuit potential" over time, which is now being measured at the first working electrode, and which corresponds to the voltage measured with high ohmic resistance between the reference electrode and the working electrode, without an external potential regulation being performed (open control circuit), is amplified by means of an instrument amplifier and it provides information on the state and the readiness to function of the first working electrode. At the same time, a voltage in the potential range II bringing about the reduction of oxygen is applied to the second working electrode via the second operational amplifier. The current conduction generated by the reduction of oxygen generates a signal proportional to the oxygen concentration at the second working electrode. If a voltage in potential range II is applied, the signal generated by the current conduction at the second working electrode always provides information on the electrolyte balance of the sensor and on the state of the separators that are arranged between the electrodes. Both signals are sent to the microcontroller and are compared with respective preset signal values there.

The three steps are the essential steps of the process. There are additional steps in preferred embodiments.

In an additional step, a voltage in the potential range I bringing about the oxidation of hydrogen is applied to the first working electrode via the first operational amplifier. The current conduction caused by the oxidation of hydrogen at the first working electrode generates a signal, which is proportional to the hydrogen concentration. A voltage in a potential range III bringing about the production of hydrogen, preferably between −1,100 mV and −800 mV, is applied to the second working electrode via the second operational amplifier. The current conduction caused by the hydrogen production at the second working electrode generates a signal proportional to the hydrogen production. Both signals are sent to the microcontroller and are compared with respective preset signal values there. A certain amount of hydrogen is always available due to the hydrogen production at the second working electrode, regardless of whether a detectable hydrogen concentration is present or not in the gas mixture to be monitored. Using the hydrogen generated, it is possible to check the readiness of the first working electrode to function with respect to the detectability of hydrogen and of the second working electrode with respect to its functional surface.

Provisions are made in an additional step for a warning signal to be sent by the microcontroller when the signal sent to the microcontroller in one of the above-described steps is outside a tolerance range specified in advance. This step does not have to follow the steps described so far in time, but it may be carried out simultaneously with them. The measured signals obtained on the basis of the current conduction are now corrected for pressure and temperature and compared with fixed, preset, allowable tolerance values. Deviations outside of the particular tolerance ranges of the signals of the first working electrode are indicative of an inacceptable hydrogen concentration in the first step, an inacceptable oxygen concentration or a defective membrane or a defective capillary in the second step, and a lack of readiness to function of the first electrode in the third step. For the second working electrode, deviations outside the tolerance range indicate defects or impairments of the electrochemical gas sensors.

Advantageous embodiments of the process are the continuous repetition of the sequence formed by the steps. Moreover, the process can be carried out with the same sequence for a second device of identical design. In case of a simultaneous performance on the two devices, it is advantageous to provide for a time offset such that the hydrogen concentration is always determined with at least one of the two devices in order to guarantee the continuous monitoring of the hydrogen concentration. Process step a) is now performed by both devices simultaneously at least until the ratio of the measured values of the two gas sensors becomes constant.

Besides the possibility of carrying out the process according to the present invention for two devices with one electrochemical gas sensor each, it is also conceivable to integrate the four working electrodes used in a single device with one electrochemical gas sensor, which comprises the four working electrodes. It would also be possible to carry out the process correspondingly with a single device that comprises an electrochemical gas sensor with three working electrodes.

An exemplary embodiment of the present invention will be explained in greater detail on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
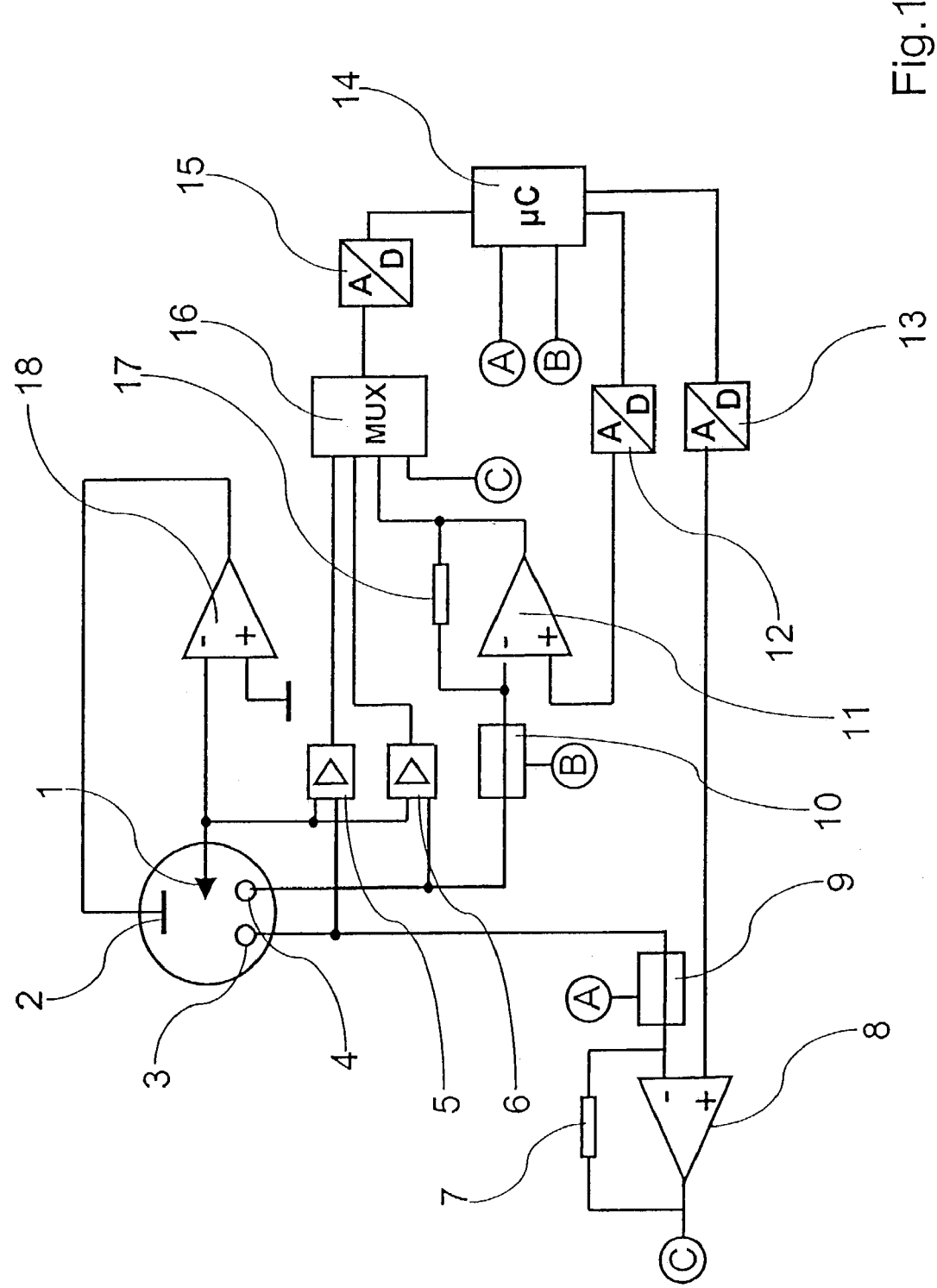
FIG. 1 is a schematic view showing a device with an electrochemical gas sensor for monitoring the hydrogen and oxygen concentrations in a gas.

Referring to the drawings in particular, FIG. 1 shows a device with an electrochemical gas sensor and a bipotentiostat 5-18 for monitoring the hydrogen and oxygen concentrations in a gas mixture. The electrochemical gas sensor comprises a first working electrode 3 and a second working electrode 4, as well as a counterelectrode 2 and a reference electrode 1. A corresponding voltage is applied to the two working electrodes 3, 4 by the bipotentiostat 5-18, which is controlled by a microcontroller 14. The bipotentiostat 5-18 comprises a first precision resistor 7, a first operational amplifier 8 and a second operational amplifier 11, a second precision resistor 17 and a third operational amplifier 18. The voltage is applied to the working electrodes 3, 4 via two circuits that have, in principle, an identical design within the device. The mode of operation of the circuits is described on the basis of the circuit for the first working electrode 3. A signal, which is converted by a first digital-analog converter 13 and is amplified by the first operational amplifier 8, with which the first precision resistor 7 is connected in parallel, is preset in the microcontroller 14. Via a downstream, closed first switch 9, the signal reaches the first working electrode 3, to which a voltage is correspondingly applied. The first switch 9 is connected to the microcontroller 14 via a line, which is shown as being interrupted in FIG. 1 with the two line terminations A for reasons of clarity. The first switch 9 is actuated by the microcontroller 14 such that it is closed when a voltage is applied to the first working electrode 3 and it is opened when the course of the open circuit potential is measured on the first working electrode 3; this corresponds to the voltage measured with a high ohmic resistance between the reference electrode and the working electrode, without an external potential regulation being performed (open circuit). The first operational amplifier 8 is connected to a multiplexer 16 via a line that is likewise shown as being interrupted by two line terminations C. The signals entering the multiplexer 16 are sent to an analog-digital converter 15 and from there to the microcontroller 14. The first working electrode 3 is located on the side of the electrochemical gas sensor facing the gas to be measured. The first working electrode 3, the reference electrode 1 and the counterelectrode 2 are connected, via the intermediary of the third operational amplifier 18, to a first instrument amplifier 5, which sends the signals to the multiplexer 16 during the measurement of the course of the open circuit potential on the working electrode 3. From there, the signals reach the microcontroller 14 via the analog-digital converter 15. A circuit fully analogous to the above-described circuit for the first working electrode 3 is provided for the second working electrode 4. A second digital-analog converter 12 sends the signals from the microcontroller 14 to the second operational amplifier 11, with which the second precision resistor 17 is connected in parallel. Via a second switch 10, which is likewise shown in the closed state in FIG. 1, the signal reaches the second working electrode 4, to which a corresponding voltage is applied. The second switch 10 is connected to the microcontroller 14 via a line shown as being interrupted at the line terminations B and can be actuated in the same manner as the first switch 9 when needed. The second operational amplifier 11 is likewise connected to the multiplexer 16. The second working electrode 4 is located on the side of the electrochemical gas sensor facing the liquid electrolyte. The second working electrode 4, the reference electrode 1 as well as the counterelectrode 2 via the third operational amplifier 18 are connected to a second instrument amplifier 6, which likewise sends the incoming signals to the multiplexer 16 for an optionally performed measurement of the course of the open circuit potential on the second working electrode 4.

Figure 2:
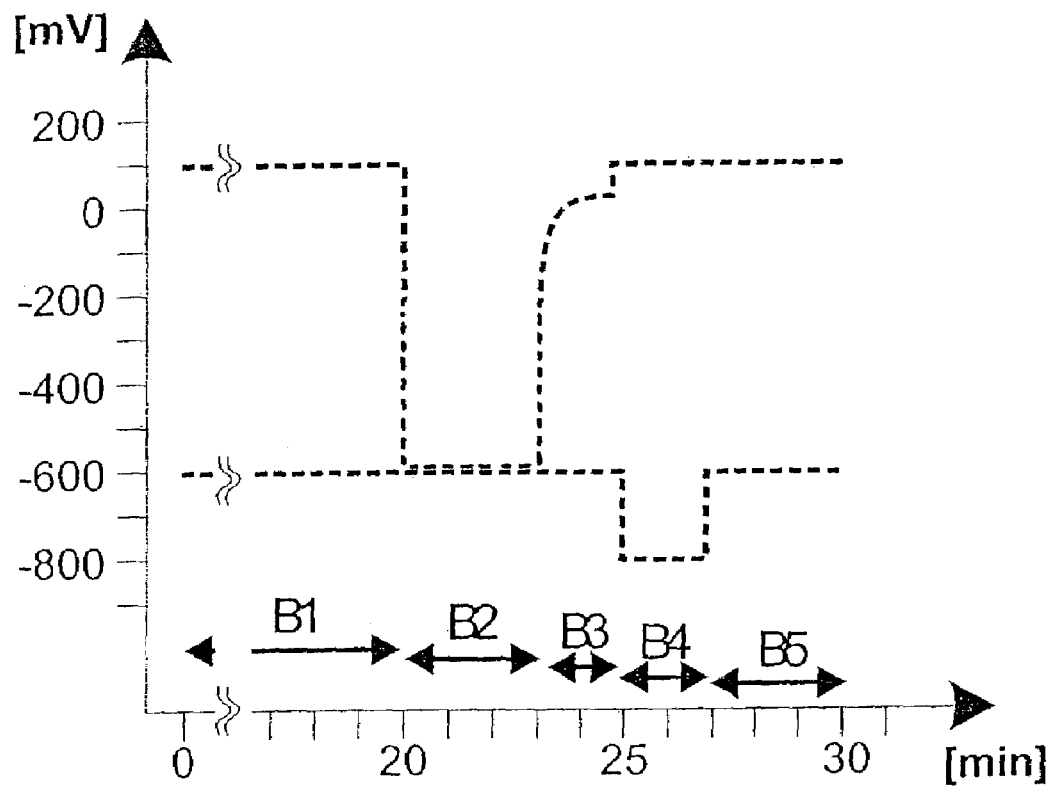
FIG. 2 is a graph showing the changes in the voltage over time at the two working electrodes of the device according to FIG. 1.

FIG. 2 shows the time course of the voltage on the first working electrode 3 and on the second working electrode 4 in millivolts [mV], as voltage is applied to them corresponding to the actuation by the microcontroller 14.

With the switches 9, 10 closed, 100 mV are present on the first working electrode 3 for determining the hydrogen concentration during the first time period B1, and −600 mV are present on the second working electrode 4 for the determination of the oxygen concentration.

In the second time period B2, a voltage of −600 mV is applied to the working electrodes 3, 4 for the determination of the oxygen concentration. This happens by actuation by the microcontroller 14. The oxygen concentration in the gas mixture is determined in this manner during the second time period B2.

During the subsequent third time period B3, the switch 9, which was hitherto closed, is actuated by the microcontroller 14 for opening. There is no external voltage on the first working electrode 3 any longer, so that the measurement of the open circuit potential, which is asymptotically approaching the value of 0 mV, can be carried out. A voltage of −600 mV continues to be present on the second working electrode 4 for determining the oxygen concentration. A voltage of 100 mV is subsequently applied to the first working electrode 3 and a voltage of −800 mV is applied to the second working electrode 4 during the fourth time period B4. Hydrogen is generated at the second working electrode 4 at a voltage of −800 mV.

In the preferred embodiment of the process according to the present invention, it is checked whether the first working electrode 3 responds sensitively to hydrogen by testing its ability to function during the fourth time period B4 by means of hydrogen generated specifically for this purpose at the second working electrode 4.

As during the first time period B1, a voltage of 100 mV is applied to the first working electrode 3 and a voltage of −600 mV is applied to the second working electrode 4 during the last time period B5. The determination of the hydrogen and oxygen concentrations in the gas mixture to be monitored is thus again possible.

In their succession, the time periods B1 through B4 form a cycle, which is repeated. B1 takes about 20 minutes, whereas the periods B2 through B4 take only a few minutes each, represented by the horizontal extension of the corresponding double arrows along the time axis, on which the time is plotted in minutes.

While specific embodiments of the invention have been shown and described in detail to illustrate the application of the principles of the invention, it will be understood that the invention may be embodied otherwise without departing from such principles.

What is claimed is:

1. A process for monitoring the hydrogen concentration in a gas mixture with at least one first device comprising an electrochemical gas sensor, the process comprising the steps of:
   a) applying a voltage to a first working electrode in a first potential range, bringing about the oxidation of hydrogen, via a first operational amplifier, applying a voltage to a second working electrode in a second potential range, bringing about the reduction of oxygen, via a second operational amplifier, measuring a current conduction proportional to the concentration of hydrogen at the first working electrode, measuring a current conduction proportional to the concentration of oxygen at the second working electrode, sending the measured current values as a signal to a microcontroller and comparing the measured values with a preset signal value at the microcontroller;
   b) applying to the two working electrodes a voltage in the second potential range, bringing about a reduction of oxygen, via the first and second operational amplifiers, measuring a current conduction proportional to the concentration of oxygen at the first and second working electrodes, sending the measured current values as a signal to the microcontroller and comparing the measured values with preset signal values at the microcontroller; and c) interrupting a connection between the first operational amplifier and the first working electrode by opening a first switch to form an open circuit, determining an open circuit potential at the first working electrode, sending the open circuit potential value as a signal to the microcontroller via an instrument amplifier, comparing the open circuit signal with preset parameters at the microcontroller, applying a voltage in the second potential range to the second working electrode, bringing about the reduction of oxygen, via the second operational amplifier, measuring a current conduction proportional to the concentration of the oxygen at the second working electrode, sending a measured current conduction as a signal to the microcontroller and comparing the current conduction signal with a preset signal value at the microcontroller.

2. A process in accordance with claim 1, further comprising the steps:

d) applying a voltage in the first potential range to the first working electrode, bringing about the oxidation of hydrogen, via the first operational amplifier) applying a voltage in a third potential range to the second working electrode, bringing about the production of hydrogen via the second operational amplifier, measuring a current conduction proportional to the concentration of the hydrogen at the first working electrode, measuring a current conduction proportional to the production of hydrogen at the second working electrode, sending the measured current conduction as a signal to the microcontroller and comparing the measured current conduction signals with a preset signal value at the microcontroller.

3. A process in accordance with claim 2, further comprising the step:

e) sending a warning signal by the microcontroller when a signal sent to the microcontroller in one of the steps a), b), c) and d) is outside a tolerance range around a preset signal set in advance far each of the steps.

4. A process in accordance with claim 2, wherein a range between −1,100 mV and −800 mV is selected as the third potential range.

5. A process in accordance with claim 1, further comprising the step:

sending a warning signal by the microcontroller when a signal sent to the microcontroller in one of the steps a), b) and c) is outside a tolerance range around a preset signal set in advance for each of the steps.

6. A process in accordance with claim 1 wherein a range between 0 mV and 200 mV is selected as the first potential range.

7. A process in accordance with claim 1, wherein a range between −700 mV and −300 mV is selected as the second potential range.

8. A process in accordance with claim 1, wherein a sequence formed from the steps a), b) and c) is continuously repeated.

9. A process in accordance with claim 8, wherein a sequence formed from the steps a), b) and c) is continuously repeated for a second device, which has the same design as the first device.

10. A process in accordance with claim 9, wherein the sequence formed from the steps is carried out offset in time for the first and second devices, so that said step a) is always being carried out in at least one of the two devices.

11. A process for monitoring hydrogen concentration in a gas mixture, the process comprising the steps of;

providing an electrochemical gas sensor with first and second working electrodes;

performing a first operation mode comprising the steps of, applying voltage to the first working electrode in a first potential range to cause oxidation of hydrogen in the sensor, applying voltage to the second working electrode in a second potential range to cause reduction of oxygen in the sensor, measuring current proportional to a concentration of hydrogen at the first working electrode and measuring current proportional to a concentration of oxygen at the second working electrode;

performing a second operation mode comprising the steps of, applying voltage to the first and second working electrodes in said second potential range to cause reduction of oxygen in the sensor, and measuring current proportional to a concentration of oxygen at the first and second working electrodes;

performing a third operation mode comprising the steps of, disconnecting the first working electrode from voltage external to the electrochemical sensor;

applying voltage to the second working electrode in said second potential range to cause reduction of oxygen in the sensor, and measuring an open circuit potential at the first working electrode and measuring current proportional to a concentration of oxygen at the second working electrode.

12. A process in accordance with claim 11, further comprising:

performing a fourth operation mode comprising the steps of, applying voltage to the first working electrode in the first potential range to cause oxidation of hydrogen in the sensor, applying voltage to the second working electrode in a third potential range to cause production of hydrogen in the sensor, measuring current proportional to a concentration of hydrogen at the first working electrode.

13. A process in accordance with claim 12, further comprising:

comparing the current measured at the first and second electrodes during said fourth mode with predetermined parameters to determine a detectability of hydrogen at the first working electrode and to determine a status of a functional surface of the second electrode.

14. A process in accordance with claim 12, further comprising:

comparing said open circuit potential with a predetermined parameter to determine a status of the first working electrode;

providing electrolyte and a separator in the electrochemical sensor;

comparing the current measured at the second electrode during said third node with a predetermined parameter to determine a status of the electrolyte and separator in the electrochemical sensor;

comparing the current measured at the first and second electrodes during said fourth mode with predetermined parameters to determine a detectability of hydrogen at the first working electrode and to determine a status of a functional surface of the second electrode, providing another electrochemical sensor with first and second working electrodes;

performing said first, second, third and fourth operation modes on said another sensor, said sensor and said another sensor being operated to have one of said sensors always performing said first mode.

15. A process in accordance with claim 11, further comprising:

comparing said open circuit potential with a predetermined parameter to determine a status of the first working electrode.

16. A process in accordance with claim 11, further comprising:

providing electrolyte and a separator in the electrochemical sensor, comparing the current measured at the second electrode during said third mode with a predetermined parameter to determine a status of the electrolyte and separator in the electrochemical sensor.

17. A process in accordance with claim 11, further comprising:

providing another electrochemical sensor with first and second working electrodes;

performing said first, second and third operation modes on said another sensor, said sensor and said another sensor being operated to have one of said sensors always performing said first mode.

18. A process in accordance with claim 11, further comprising:

comparing said currents and said open circuit potential with predetermined tolerance ranges;

generating a warning signal when one of said currents and said open circuit potential are outside said tolerance range.

19. A device for monitoring hydrogen concentration in a gas mixture, the device comprising:

an electrochemical gas sensor with first and second working electrodes;

a controller operating in a first mode to apply voltage to said first working electrode in a first potential range to cause oxidation of hydrogen in said sensor, to apply voltage to said second working electrode in a second potential range to cause reduction of oxygen in said sensor, to measure current proportional to a concentration of hydrogen at said first working electrode and to measure current proportional to a concentration of oxygen at said second working electrode, said controller operating in a second mode to apply voltage to said first and second working electrode in said second potential range to cause reduction of oxygen in said sensor, and to measure current proportional to a concentration of oxygen at said first and second working electrodes, said controller operating in a third mode to disconnect said first working electrode from voltage external to said electrochemical sensor, to apply voltage to said second working electrode in said second potential range to cause deduction of oxygen in said sensor, to measure an open circuit potential at said first working electrode and to measure current proportional to a concentration of oxygen at said second working electrode.

20. A device in accordance with claim 19, further comprising:

another electrochemical sensor with first and second working electrodes, said controller performing said first, second and third operation modes on said another sensor said controller operating said sensor and said another sensor to have one of said sensors always performing said first mode.

* * * * *